United States Patent
Costello

(10) Patent No.: US 10,292,846 B2
(45) Date of Patent: May 21, 2019

(54) CONTROL SYSTEM FOR A STENT DELIVERY SYSTEM

(75) Inventor: Kieran Costello, Ballina-Killaloe (IE)

(73) Assignee: Cook Medical Technologies LLC, Bloomington, IN (US)

( * ) Notice: Subject to any disclaimer, the term of this patent is extended or adjusted under 35 U.S.C. 154(b) by 601 days.

(21) Appl. No.: 13/181,075

(22) Filed: Jul. 12, 2011

(65) Prior Publication Data

US 2012/0022631 A1 Jan. 26, 2012

Related U.S. Application Data

(60) Provisional application No. 61/366,228, filed on Jul. 21, 2010.

(51) Int. Cl.
*A61F 2/84* (2006.01)
*A61F 2/95* (2013.01)
(Continued)

(52) U.S. Cl.
CPC ............... *A61F 2/95* (2013.01); *A61F 2/966* (2013.01); *A61F 2002/9511* (2013.01);
(Continued)

(58) Field of Classification Search
CPC .......... A61F 2/954; A61F 2/962; A61F 2/966; A61F 2002/9517; A61F 2002/9528;
(Continued)

(56) References Cited

U.S. PATENT DOCUMENTS 3,888,258 A * 6/1975 Akiyama ................. 606/109
5,415,664 A * 5/1995 Pinchuk .................. A61F 2/95
604/523
(Continued)

FOREIGN PATENT DOCUMENTS

EP 1 891 914 A1 2/2008
WO WO 95/11055 A1 4/1995
(Continued)

OTHER PUBLICATIONS

International Search Report dated Nov. 9, 2011 for International Application No. PCT/US2011/043720.
(Continued)

*Primary Examiner* — Julie A Szpira
(74) *Attorney, Agent, or Firm* — Brinks Gilson & Lione

(57) ABSTRACT

A control system for controlling movement of a stent delivery system, a stent delivery system and a method for controlling movement of a stent delivery system are provided. The control system includes a housing having a chamber formed therein, a first drive at least partially positioned within the housing and operably connected to the first shaft of the delivery system and a second drive at least partially positioned within the housing and operably connected to the second shaft. The control system also includes a pressure controller operably connected to the housing and configured to change the pressure within the chamber. The first drive and the second drives are movable in response to the pressure change within the chamber and movement of the second drive relative to the first drive causes the second shaft to move relative to the first shaft to expand or constrain a stent operably connected thereto.

15 Claims, 7 Drawing Sheets

(51) Int. Cl.
*A61F 2/966* (2013.01)
*A61M 25/00* (2006.01)
*A61M 25/01* (2006.01)

(52) U.S. Cl.
CPC ............... *A61F 2002/9517* (2013.01); *A61M 2025/0006* (2013.01); *A61M 2025/0175* (2013.01)

(58) Field of Classification Search
CPC .... A61F 2002/9534; A61F 2/95; A61F 2/958; A61F 2/97; A61F 2002/9505; A61F 2002/9511; A61F 2002/9522; A61F 2002/9583
USPC ........................................ 623/1.1–1.11, 1.23
See application file for complete search history.

(56) References Cited

U.S. PATENT DOCUMENTS

| | | | |
|---|---|---|---|
| 5,474,563 A | 12/1995 | Myler et al. | |
| 5,910,144 A * | 6/1999 | Hayashi | A61B 17/221 606/108 |
| 6,113,608 A * | 9/2000 | Monroe | A61F 2/966 604/264 |
| 6,709,667 B1 * | 3/2004 | Lowe | A61F 6/18 424/422 |
| 7,384,420 B2 | 6/2008 | Dycus et al. | |
| 7,632,298 B2 * | 12/2009 | Hijlkema | A61F 2/95 606/194 |
| 8,512,401 B2 * | 8/2013 | Murray et al. | 623/2.11 |
| 2002/0045929 A1 | 4/2002 | Diaz | |
| 2003/0191516 A1 * | 10/2003 | Weldon et al. | 623/1.12 |
| 2005/0033402 A1 | 2/2005 | Cully et al. | |
| 2006/0204556 A1 * | 9/2006 | Daniels et al. | 424/443 |
| 2007/0118079 A1 * | 5/2007 | Moberg | A61F 2/95 604/164.07 |
| 2007/0233222 A1 * | 10/2007 | Roeder | A61F 2/95 623/1.11 |
| 2007/0293934 A1 * | 12/2007 | Grewe | 623/1.12 |
| 2009/0024133 A1 * | 1/2009 | Keady et al. | 606/99 |
| 2009/0024137 A1 * | 1/2009 | Chuter | A61F 2/95 606/108 |
| 2009/0312832 A1 * | 12/2009 | Delap | A61F 2/95 623/1.11 |
| 2010/0234933 A1 * | 9/2010 | Punga | A61F 2/95 623/1.12 |

FOREIGN PATENT DOCUMENTS

| | | |
|---|---|---|
| WO | WO 00/18330 A1 | 4/2000 |
| WO | WO 2006/012421 A2 | 2/2006 |

OTHER PUBLICATIONS

Written Opinion dated Nov. 9, 2011 for International Application No. PCT/US2011/043720.

* cited by examiner

CONTROL SYSTEM FOR A STENT DELIVERY SYSTEM

RELATED APPLICATIONS

This application claims the benefit of U.S. Provisional Application No. 61/366,228, filed Jul. 21, 2010, which is incorporated by reference herein in its entirety.

TECHNICAL FIELD

This invention relates to a medical device and, in particular to a control system for a device for delivering and deploying a stent and a method of controlling the stent delivery system.

BACKGROUND

A self-expanding stent is typically introduced into the body using a delivery device that includes an outer sheath coaxially disposed and slidable over an inner catheter. The stent is disposed at the distal end of the device between the inner catheter and the outer sheath and held in a compressed position by the outer sheath. The inner catheter and the outer sheath move coaxially with respect to each other. The stent may be deployed by proximally pulling back the outer sheath relative to the inner catheter until the stent is exposed. The self-expanding stent expands from the stent distal end to the stent proximal end as the sheath is proximally withdrawn.

Several problems may occur with the sheathed delivery device described above. The sheath release delivery devices are difficult to reposition or remove and slow to operate. The stent may only be partially deployed prior to reconstrainment of the stent by the sheath in order to still reposition or remove the stent. Once the stent is fully deployed, i.e. radially expanded, the sheath cannot reconstrain the stent. For example, utilizing a conventional outer sheath/inner catheter delivery device may cause the physician to inadvertently use excessive force and pull back the outer sheath too far, thereby prematurely deploying the stent in an incorrect position within a body lumen. At this step in the procedure, repositioning of the stent becomes difficult, if not impossible, because the stent has already radially self-expanded into the body lumen.

Additionally, in a typical sheath release device where the outer sheath is proximally withdrawn, the first portion of the self-expanding stent to make contact with the body vessel is the most distal portion of the stent. This type of release may cause difficulty in accurately placing the proximal portion of the stent because the distal end of the stent is positioned first while the proximal portion of the stent is still covered by the outer sheath. Accurate placement of the proximal portion of the stent and/or the stent body may be important in certain applications, for example to prevent stent migration or to properly open a stricture along the entire length of the stricture. An additional drawback occurs with the sheathed stent delivery system where direct visualization of the stent is required. For example, in endoscopically placed stents, the sheath tends to prevent or obscure the location of the stent, making accurate placement of the stent more difficult.

Further potential drawbacks for the conventional sheathed stent delivery system involve the stent placement within the system prior to use within a patient. Loading and anchoring of a conventional sheathed stent delivery device is an involved process that may require preloading the stent into the device so that the stent remains compressed within the sheath during shipment and storage prior to use in the patient. Extended compression of the stent may lead to an alteration in the stent mechanical properties.

Conventional sheathed stent delivery devices also require a high force to overcome the friction between the stent and the sheath that may also be a problem for proper stent placement within the patient. The introducer must be mechanically stronger to overcome the frictional forces to avoid undesirable frictional consequences such as stretching of the introducer catheters and hysteresis in the movement of the stent. The sheathed stent delivery device also requires more space within an endoscope compared to a sheathless device and also adds additional expense to the delivery system.

A longitudinally tensioned stent delivery system has been developed to avoid some of the drawbacks that can occur with a sheathed delivery device described above. The longitudinally tensioned stent delivery system includes an inner and an outer shaft coaxially positioned and longitudinally moveable in relation to each other to expand and constrain a stent positioned on the inner and outer shafts that can increase the control, accuracy and ease of placement of a stent during deployment of the stent within a patient. A control mechanism for controlling the movement of the inner and outer shafts relative to each other is needed to control the longitudinally tensioned stent delivery system to provide the ability to deliver the stent to the desired position and to be able to reconstrain, recapture, reposition and/or remove the stent after expansion of the stent.

SUMMARY OF THE INVENTION

Accordingly, it is an object of the present invention to provide a device and a method having features that resolve or improve on one or more of the above-described drawbacks.

The foregoing object is obtained in one aspect of the present invention by providing a control system for a stent delivery system having a first shaft and a second shaft movable relative to the first shaft. The control system includes a housing having a chamber formed therein, a first drive at least partially positioned within the housing and operably connected to the first shaft of the delivery system and a second drive at least partially positioned within the housing and operably connected to the second shaft. The control system also includes a pressure controller operably connected to the housing and configured to change the pressure within the chamber. The first drive and the second drives are movable in response to the pressure change within the chamber and the movement of the second drive relative to the first drive causes the second shaft to move relative to the first shaft so as to expand or constrain a stent operably connected thereto.

In another aspect of the present invention, a stent delivery system is provided. The stent delivery system includes a first shaft, a second shaft movable relative to the first shaft and coaxially extending with the first shaft, a stent operably connected to the first shaft and the second shaft, and a control system. The control system includes a housing having a chamber formed therein, a first drive at least partially positioned within the housing and operably connected to the first shaft of the delivery system and a second drive at least partially positioned within the housing and operably connected to the second shaft. The control system also includes a pressure controller operably connected to the housing and configured to change the pressure within the chamber and to move the second drive and the second shaft relative to the first drive and the first shaft.

In another aspect of the present invention, a method for implanting a stent using a stent delivery system is provided. The method includes providing a control system, the control system including a housing having a chamber formed therein, a first drive at least partially positioned within the housing and operably connected to the first shaft of the delivery system and a second drive at least partially positioned within the housing and operably connected to the second shaft. The control system also includes a pressure controller operably connected to the housing. The method further includes changing the pressure applied to the chamber using the pressure controller, moving the second drive and the second shaft in response to the pressure change and changing the position of the first shaft relative to the second shaft.

DETAILED DESCRIPTION OF THE EMBODIMENTS

Figure 1A:
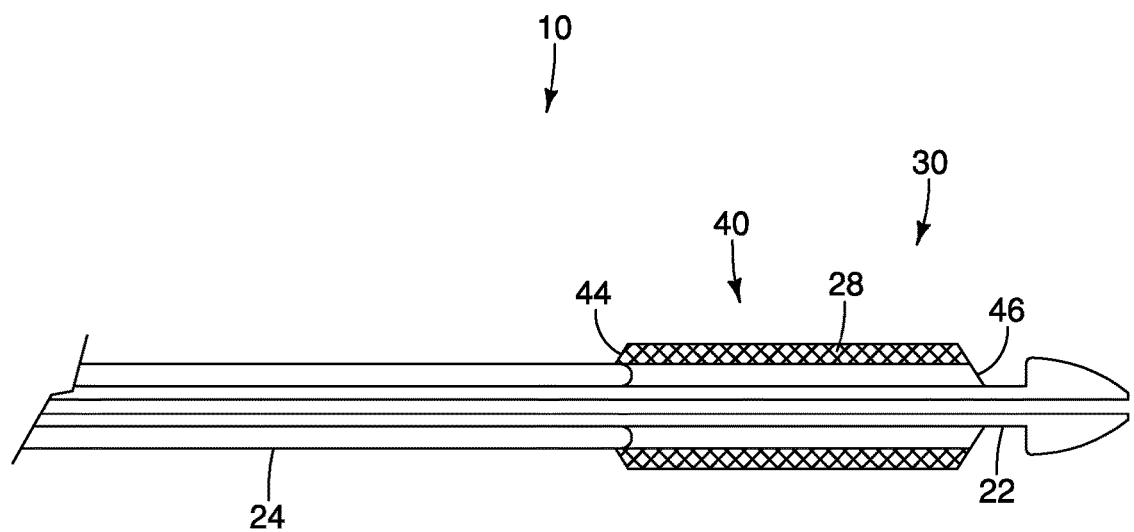
FIG. 1A is a sectional view of a distal portion of a stent delivery system showing the stent in a constrained configuration.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the stent to a patient. Hence the term "distal" means the portion of the delivery system that is farthest from the physician and the term "proximal" means the portion of the delivery system that is nearest to the physician.

Figure 1B:
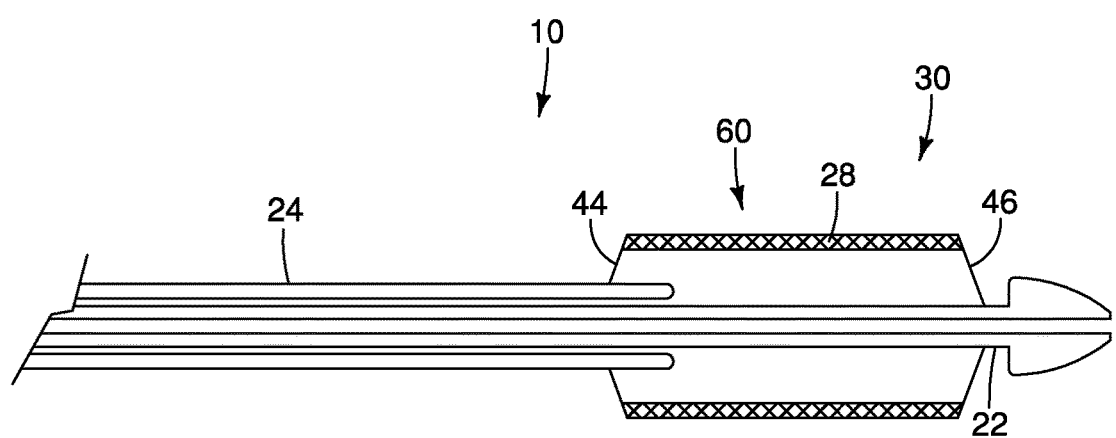
FIG. 1B is a sectional view of the device shown in FIG. 1A showing the stent in an expanded configuration.

FIGS. 1A and 1B illustrate a distal portion 30 of an exemplary stent delivery system 10 that may be driven by a control system in accordance with embodiments of the present invention. The stent delivery system 10 includes an inner shaft 22 and an outer shaft 24 that are longitudinally movable with respect to each other to facilitate placement of a stent 28. The stent 28 may be connected to the inner shaft 22 by a distal constraining member 46 and to the outer shaft 24 by a proximal constraining member 44. The stent 28 is movable between a constrained configuration 40 shown in FIG. 1A and an expanded configuration 60 shown in FIG. 1B. As shown in FIG. 1A, the inner shaft 22 is moved distally and the outer shaft 24 is moved proximally to position the stent 28 in the constrained configuration 40. As shown in FIG. 1B, the inner shaft 22 is moved proximally and the outer shaft 24 is moved distally to expand the stent 28 from the constrained configuration 40 to the expanded configuration 60.

Figure 1C:
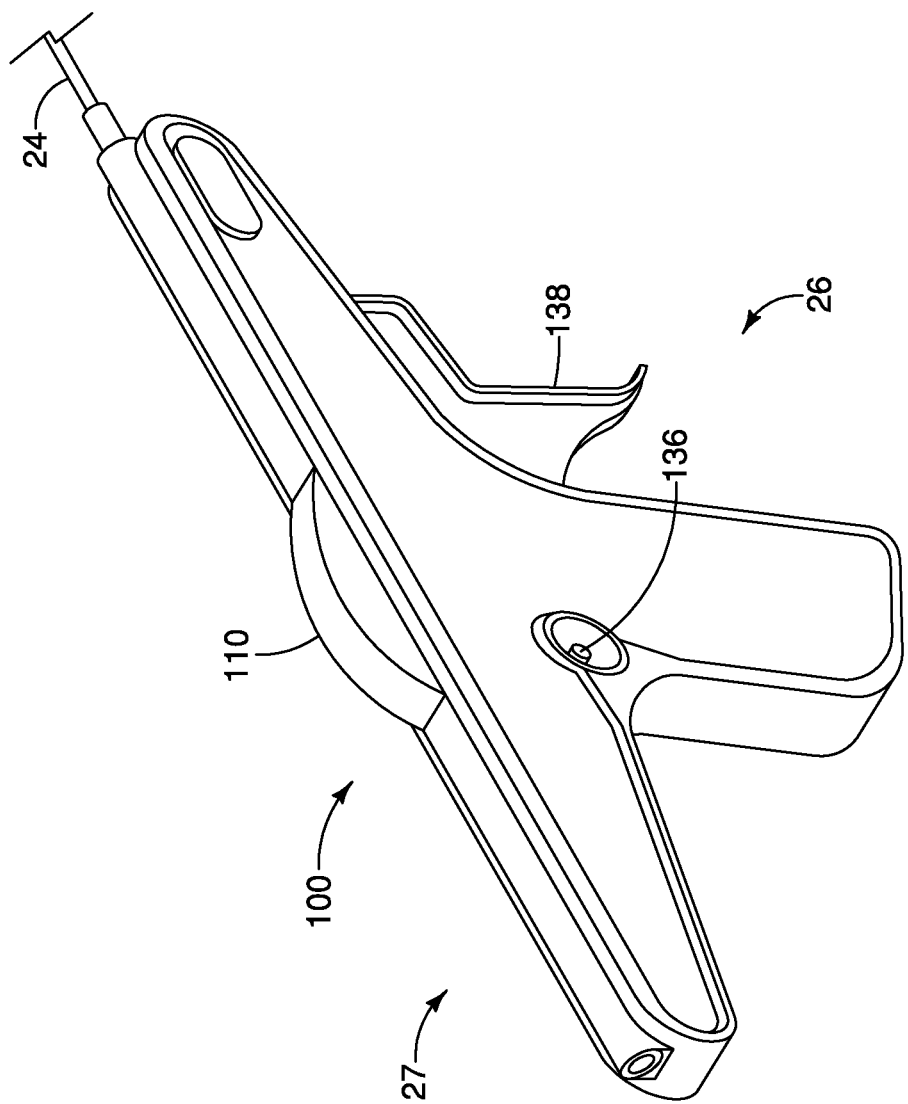
FIG. 1C is a perspective view of a handle for the stent delivery system shown in FIG. 1A.
Figure 2:
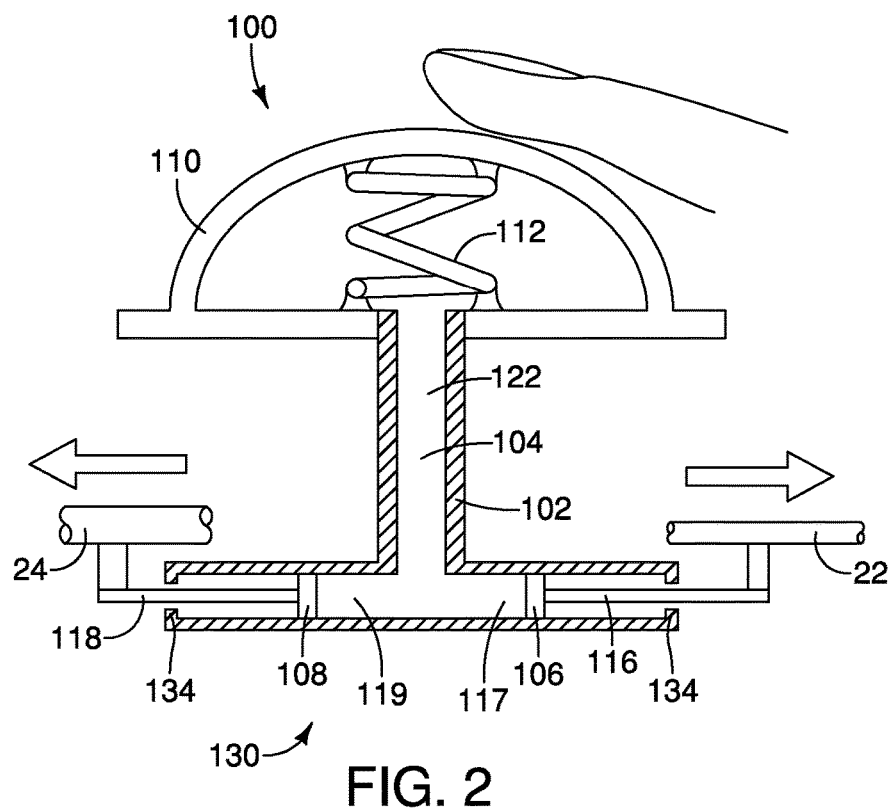
FIG. 2 is a sectional view of a control mechanism according to an embodiment of the present invention.

An embodiment of a control system 100 is shown in FIG. 2. The control system 100 may be provided as part of a handle 26 at a proximal portion 27 of the stent delivery system 10 (See FIG. 1C showing an exemplary handle 26.) As shown in FIG. 2, the control system 100 includes a housing 102 having a chamber 104 formed therein. A first drive 106 is at least partially positioned within the housing 102 and operably connected to the inner shaft 22. A second drive 108 is also at least partially positioned within the housing 102 and operably connected to the outer shaft 24. The inner shaft 22 extends coaxially through the outer shaft 24 as shown in FIGS. 1A and 1B, but both the inner shaft 22 and the outer shaft 24 are shown truncated for clarity in FIGS. 2 and 3. A pressure controller 110 is operably connected to the housing 102 and the chamber 104 and generates a pressure change within the chamber 104 to move the drives 106, 108. In some embodiments, the first and second drives 106, 108 are movable in substantially equal and opposite directions to control the movement of the outer shaft 24 relative to the inner shaft 22 so that the longitudinal tension of the stent 28 is applied or removed with substantially equal force on both ends of the stent 28. In other embodiments, one of the first drive 106 or the second drive 108 may be fixed in position so that the inner shaft 22 or the outer shaft 24 is fixed in position and the other of the first drive 106 or the second drive 108 is movable so that the inner shaft or the outer shaft is movable to longitudinally tension and un-tension the stent 28. By way of non-limiting example, the pressure controller 110 may be provided as a flexible membrane as shown in FIG. 2. Other types of pressure controllers may also be used, including, but not limited to, syringes and balloons as described below.

The control system 100 may further include a first arm 116 connected to the first drive 106 and the inner shaft 22. The first arm 116 is movable with the first drive 106 in response to the pressure change within the chamber 104. The first drive 106 is provided within a first section 117 of the housing 102 such that the first drive 106 forms a seal against the housing 102 and encloses the first section 117 of the housing 104. A second arm 118 is connected to the second drive 108 and the outer shaft and that is movable with the second drive 108 in response to the change in pressure within the chamber 104. The second drive 108 is provided within a second section 119 of the housing 104 and may provide a seal against the housing 102. The housing 102 includes a third section 122 that is operably connected to the pressure controller 110. Together the first drive 106, the second drive 108 and the pressure controller 110 form the sealed chamber 104. The chamber 104 may be air-filled or fluid-filled. A biasing member 112 may optionally be provided with the control system 100 for biasing the flexible member 110.

Figure 3:
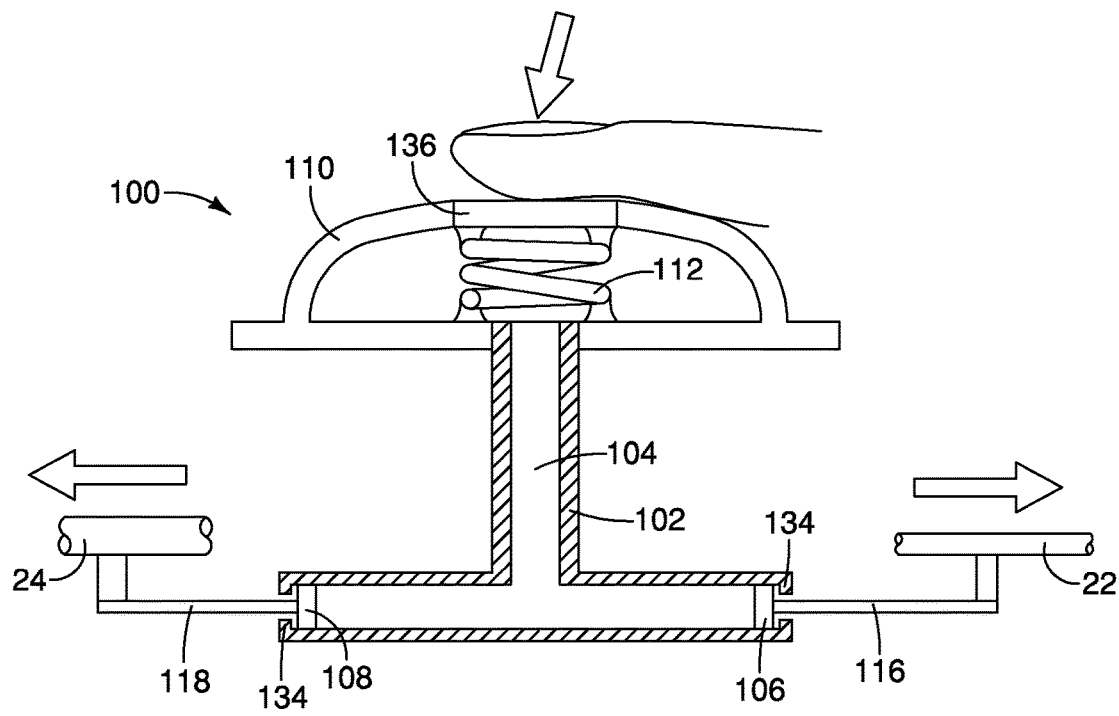
FIG. 3 is a sectional view of the control mechanism shown in FIG. 2 in a second position.

As shown in FIG. 2, external pressure may be exerted on the flexible membrane 110, for example by the operator's thumb, to provide pressure against the first and second drives 106, 108 to move the first and second drives 106, 108 from a first position 130 to a second position 140 shown in FIG. 3 with a single-handed operation. The first position 130 for the control system 100 corresponds to the expanded configuration 60 of the stent 28 shown in FIG. 1B. In the first position 130, the flexible membrane 110 is fully expanded and the first and second drives 106, 108 are positioned within the first and second section 117, 119 of the housing 102 so that the drives 106, 108 are positioned relatively close together. As shown in FIG. 3, the flexible membrane 110 is compressed forcing the air or fluid within the chamber 104 to press against the first and second drives 106, 108 so that the first and second drives 106, 108 move apart so that the first drive moves distally 106 and the second drive 108 moves proximally. The movement of the first and second drives 106, 108 moves the inner shaft 22 and outer shaft 24 in opposite directions to place longitudinal tension on the stent 28 and collapse the stent 28 into the constrained configuration 40 shown in FIG. 1A. As indicated by the arrows in FIG. 3, the inner shaft 22 is moved distally and the outer shaft 24 is moved proximally to longitudinally tension the stent 28. In some embodiments, the inner shaft 22 may be connected to the second drive 108 and the outer shaft may be connected to the first drive 106 so that the first and second drives 106, 108 move the inner shaft 22 and outer shaft 24 in opposite directions (the inner shaft 22 moves proximally and the outer shaft 24 moves distally) to release the longitudinal tension on the stent 28 to expand the stent 28 into the expanded configuration 60 when the flexible membrane 110 is compressed.

The first and second sections 117, 119 of the housing 102 may each include a stop 134 that prevents the first and second drives 106, 108 from over tensioning the stent 28. The stops 134 may be calibrated so that the optimal longitudinal tension is placed on the stent 28 when the first and second drives 106, 108 are pressed against the stop 134. In addition, the control system 100 may include a releasable lock 136 that holds the control system 100 in the second position 140 until the stent delivery system 10 is in position within a patient's lumen and the stent 28 is in a position to be moved to the expanded configuration 60. The releasable lock 136 may hold the biasing member 112 compressed so that the first and second drives 106, 108 are held against stops 134. Alternatively, a locking mechanism 138 may be provided on the handle 26 as shown in FIG. 1C or a trigger 138 may be used to hold the inner shaft 22 and the outer shaft 24 in a fixed position relative to each other until the stent 28 is ready to be expanded. Any type of locking mechanism may be used to releasably lock the control system 100 in the first configuration 130 and the second configuration 140 as will be understood by one skilled in the art.

Figure 4:
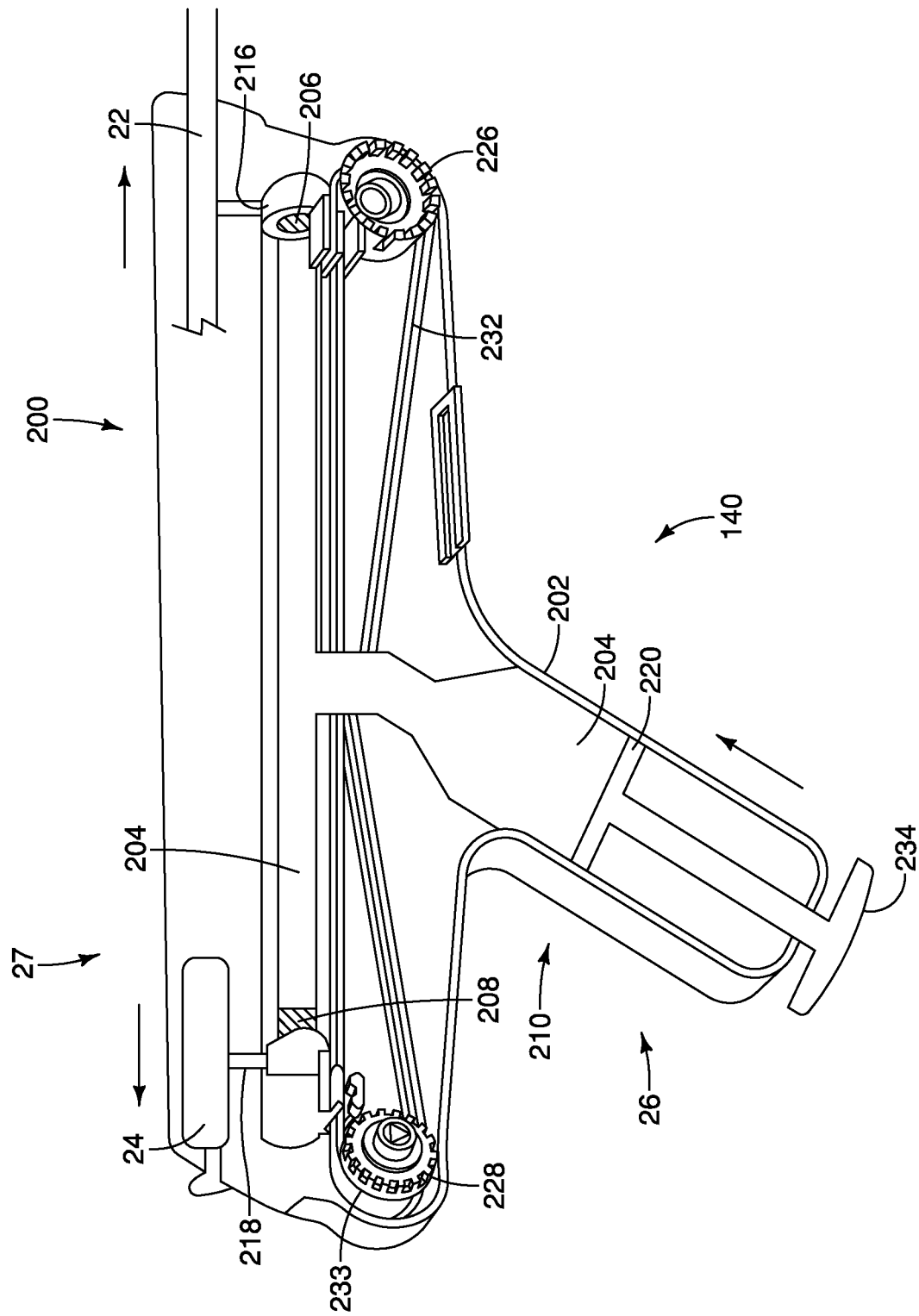
FIG. 4 is a sectional view of an embodiment of a control mechanism according to an embodiment of the present invention.

An embodiment of a control system 200 is shown in FIG. 4. The control system 200 is shown provided as part of the handle 26 at the proximal portion 27 of the stent delivery system 10. The control system 200 includes a housing 202 having a chamber 204 formed therein and positioned within the handle 26. A first drive 206 is operably connected to the inner shaft 22 and the chamber 204. A second drive 208 is operably connected to the outer shaft 24 and the chamber 204. The inner shaft 22 extends coaxially through the outer shaft 24 as shown in FIGS. 1A and 1B, but both the inner shaft 22 and the outer shaft 24 are shown truncated for clarity in FIG. 4. A pressure controller 210 provided in the form of a syringe is operably connected to the housing 202 and the chamber 204 and is movable to generate a pressure within the chamber 204. The first drive 206 and the second drive 208 are movable in opposite directions in response to movement of the syringe 210 to change the pressure within the chamber 204 of the housing 202.

The first drive 206 and the second drive 208 are movable within the chamber 204 in response to the pressure change within the chamber 204. The syringe 210 includes a drive 220. Together the first drive 206, the second drive 208 and the third drive 220 of the syringe 210 form the sealed chamber 204 within the housing 202. The drives 206, 208, 220 may be provided as pistons having a sealing fit within the housing 202 and that are slidable within the housing 202 in response to changes in pressure with the chamber 204. The chamber 204 may be air-filled or fluid-filled.

The control system 200 further includes a first gear 226 and a second gear 228. The first gear 226 is operably connected to the first drive 206 and the second gear 228 is operably connected to the second drive 208. A belt 232 connects the first and second gears 226, 228 so that the movement of the first and second drives 206, 208 is substantially equal. In the event that there is a difference in the friction against the drives 206, 208, the belt 232 and gears 226, 228 will minimize any difference in the movement of the drives 206, 208. An idler gear 233 may be included on either the first or second drive 206, 208 to change the direction of the motion of the belt 232 and allow the drives 206, 208 to move in the opposite direction.

As shown in FIG. 4, external pressure may be exerted on a plunger 234 of the syringe 210 to increase the pressure against the first and second drives 206, 208 to move the first and second drives 206, 208 from a first position 130 with the drives 206, 208 positioned relatively closer together (see for example FIG. 2) to a second position 140 shown in FIG. 4 with a single-handed operation. The first position 130 for the control system 200 corresponds to the expanded configuration 60 of the stent 28 shown in FIG. 1B. In the first position 130, the plunger 234 of the syringe 210 is fully withdrawn in the housing 202 and the first and second drives 206, 208 are positioned relatively close together. As shown in FIG. 4, the plunger 234 has been depressed and the third drive 220 is moved into the chamber 204 forcing the air or fluid within the chamber 204 to press against the first and second drives 206, 208 so that the first and second drives 206, 208 move apart and move the inner shaft 22 and outer shaft 24 in opposite directions to place longitudinal tension on the stent 28 and collapse the stent 28 into the constrained configuration 40 shown in FIG. 1A.

As indicated by the arrows in FIG. 4, the inner shaft 22 is moved distally and the outer shaft 24 is moved proximally and the stent 28 is longitudinally tensioned. The stent 28 may be moved to the expanded configuration 60 by withdrawing the plunger 234 in the housing 202 to create a negative pressure on the drives 206, 208 that pulls the drives 206, 208 closer together and thus moving the inner shaft 22 proximally and the outer shaft 24 distally to expand the stent 28. The stent 28 may be repeatedly moved between the constrained configuration 40 and the expanded configuration 60 by movement of the plunger 234 and drive 220 within the housing 202 to change the pressure within the chamber 204. In some embodiments, a trigger may replace the plunger 234 to control the movement of the third drive 220 within the housing 202. (Not shown.). In some embodiments, the inner shaft 22 may be connected to the second drive 208 and the outer shaft 24 may be connected to the first drive 206 so that the first and second drives 206, 208 move the inner shaft 22 and outer shaft 24 in opposite directions (the inner shaft 22 moves proximally and the outer shaft 24 moves distally) to release the longitudinal tension on the stent 28 to expand the stent 28 into the expanded configuration 60 when the plunger 234 is depressed.

Similar to the control system 100 described above, the control system 200 may include stops for limiting the opposite movement of the inner and outer shafts 22, 24 to control the amount of longitudinal tension on the stent 28 in the constrained configuration 40. The control system 200 may also include a locking mechanism to releasably lock the control system in the first position 130 or the second position 140.

Figure 5:
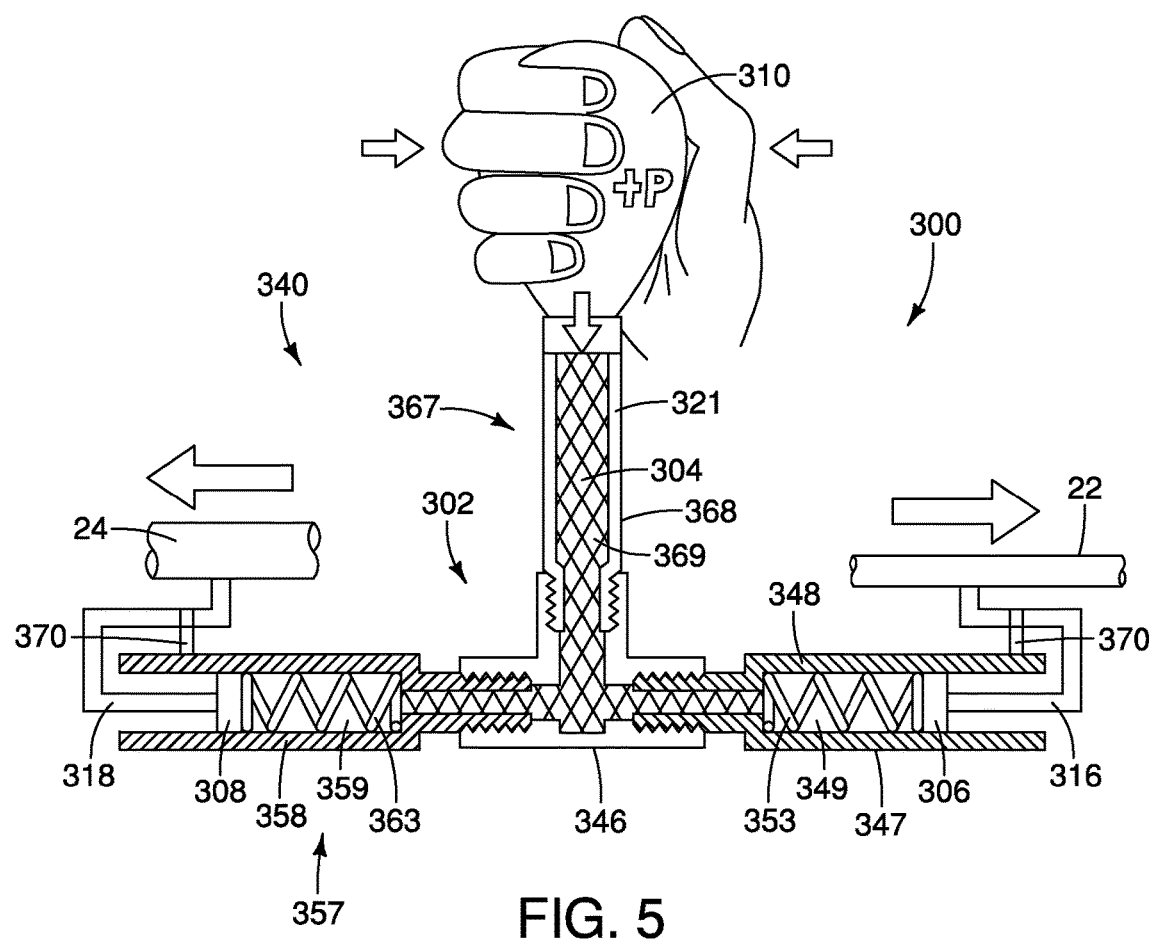
FIG. 5 is a sectional view of an embodiment of a control mechanism according to an embodiment of the present invention.
Figure 6:
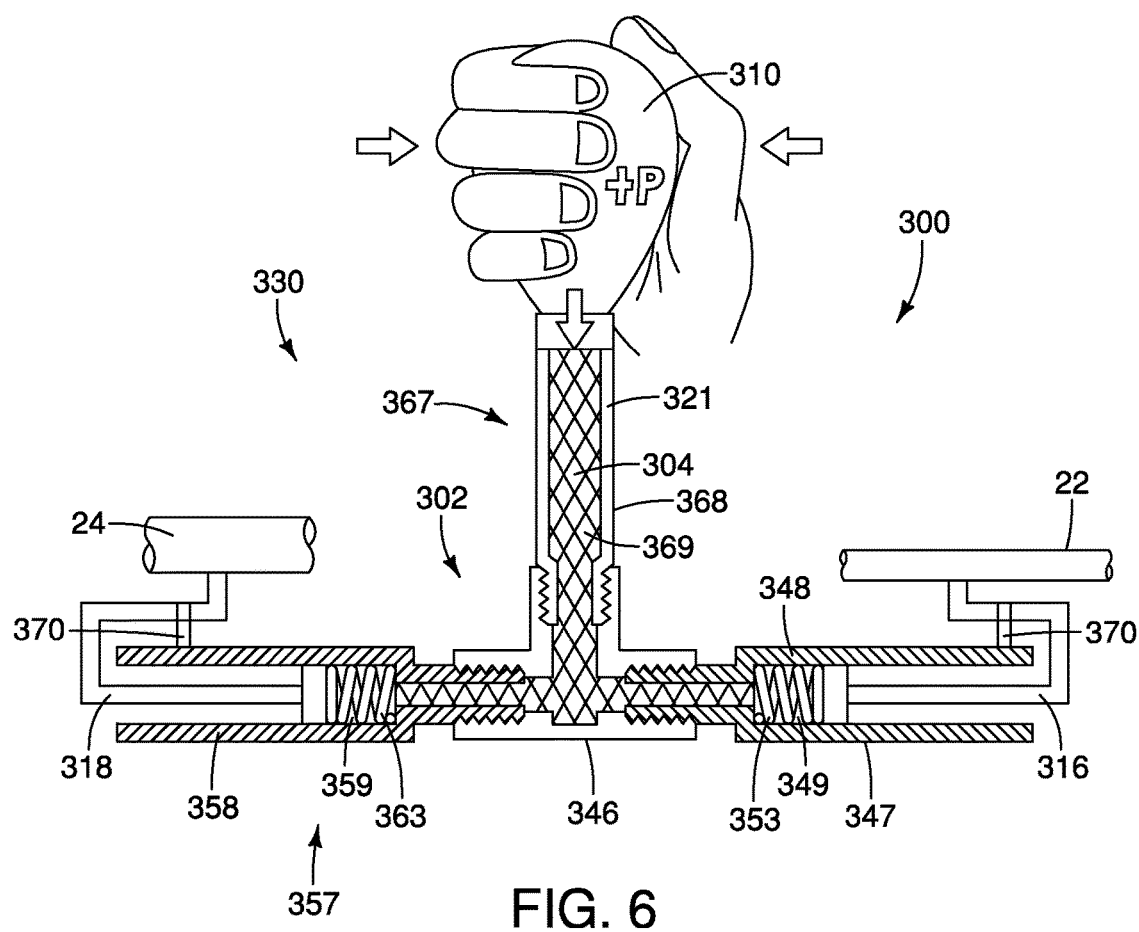
FIG. 6 is a sectional view of the control mechanism shown in FIG. 5 in a second position.

An embodiment of a control system 300 is shown in FIGS. 5 and 6. The control system 300 may be provided as part of the handle 26 at the proximal portion 27 of the stent delivery system 10. The control system 300 includes a housing 302 having a chamber 304 formed therein. As shown in FIG. 5, the housing 302 may be formed from separate components and connected together, for example using a T-connector 346. Alternatively, the housing 302 may be formed from a single component. The housing 304 includes a first housing portion 347 having a barrel 348 and a chamber 349 formed within the barrel 348. A first drive 306 forming a seal against the barrel 348 is movably positioned within the barrel 348 and operably connected to the inner shaft 22. A first biasing member 353 may be provided in the first housing portion 347. The housing 304 includes a second housing portion 357 having a barrel 358 and a chamber 359 formed within the barrel 358. A second drive 308 forming a seal against the barrel 358 is movably positioned within the barrel 358 and is operably connected to the outer shaft 24. A second biasing member 363 may be provided in the second housing portion 357. The inner shaft 22 extends coaxially through the outer shaft 24 as shown in FIGS. 1A and 1B, but both the inner shaft 22 and the outer shaft 24 are shown truncated for clarity in FIG. 5. The housing 304 further includes a third housing portion 367 having a barrel 368 and a chamber 369 formed within the barrel 368. The housing portions 347, 357, 367 are connected via the T-connector 346 and the chambers 349, 359, 369 are connected together to form the chamber 304. The connection of the housing portions 347, 357, 367 to the T-connector 346 may be through a threaded connection, a luer-type connection or any connection suitable to form a sealed chamber 304 within the housing 302. The chamber 304 may be fluid-filled or air-filled.

A pressure controller 310 provided in the form of a balloon device is operably connected to the housing portion 367. The pressure controller 310 may also be provided as a syringe or a flexible membrane or other pressure generating member and be used with the control system 300. Similar to the embodiments described above, the first drive 306 and the second drive 308 are movable in opposite directions in response to movement of the balloon device 310 to change the pressure within the chamber 304 of the housing 302. As the operator squeezes inward on the balloon device 310 the pressure against the first and second drives 306, 308 moves the first and second drives 306, 308 with a single-handed operation. In some embodiments, the movement of the first and second drives 306, 308 is in substantially equal and opposite directions.

As shown in FIG. 5, the biasing members 353, 363 may be provided as tension springs so that the biasing members 353, 363 are loaded when pressure is applied to the chamber 304 and the first drive 306 and second drive 308 move apart from each other to a second position 340. Applying pressure to the balloon device 310 forces the air or fluid within the chamber 304 to press against the first and second drives 306, 308 so that the first and second drives 306, 308 move apart and move the inner shaft 22 and outer shaft 24 in opposite directions to place longitudinal tension on the stent 28 and collapse the stent 28 into the constrained configuration 40 shown in FIG. 1A. As indicated by the arrows in FIG. 5, the inner shaft 22 is moved distally and the outer shaft 24 is moved proximally and the stent 28 is longitudinally tensioned. A releasable lock member 370 may be included to lock the inner shaft 22 and the outer shaft 24 in position to hold the stent in the constrained configuration 40 or the expanded configuration 60.

The stent 28 may be moved to the expanded configuration 60 by releasing the pressure on the balloon member 310 in the housing 302, the biasing members 353, 363 are returned to the unloaded position and the drives 306, 308 are moved closer together to a first position 330 as shown in FIG. 6. The biasing members 353, 363 facilitate the movement of the drives 306, 308 inward to move the inner shaft 22 proximally and the outer shaft 24 distally to bring the stent 28 to the expanded configuration 60. The stent 28 may be repeatedly moved between the constrained configuration 40 and the expanded configuration 60 by changing the pressure on the balloon member 310 to change the pressure within the chamber 304. The control system 300 may also be provided with biasing members 353, 363 in the form compression springs. As one skilled in the art would understand, compression springs would be positioned on the other side of the drives 306, 308 than shown in FIGS. 5 and 6 to bias the drives toward each other in the absence of pressure from the pressure controller 310.

In some embodiments, the inner shaft 22 may be connected to the second drive 308 and the outer shaft may be connected to the first drive 306 so that the first and second drives 306, 308 move the inner shaft 22 and outer shaft 24 in opposite directions to those described above.

Similar to the control system 100 described above, the control system 300 may include stops for limiting the opposite movement of the inner and outer shafts 22, 24 to control the amount of longitudinal tension on the stent 28 in the constrained configuration 40.

Figure 7:
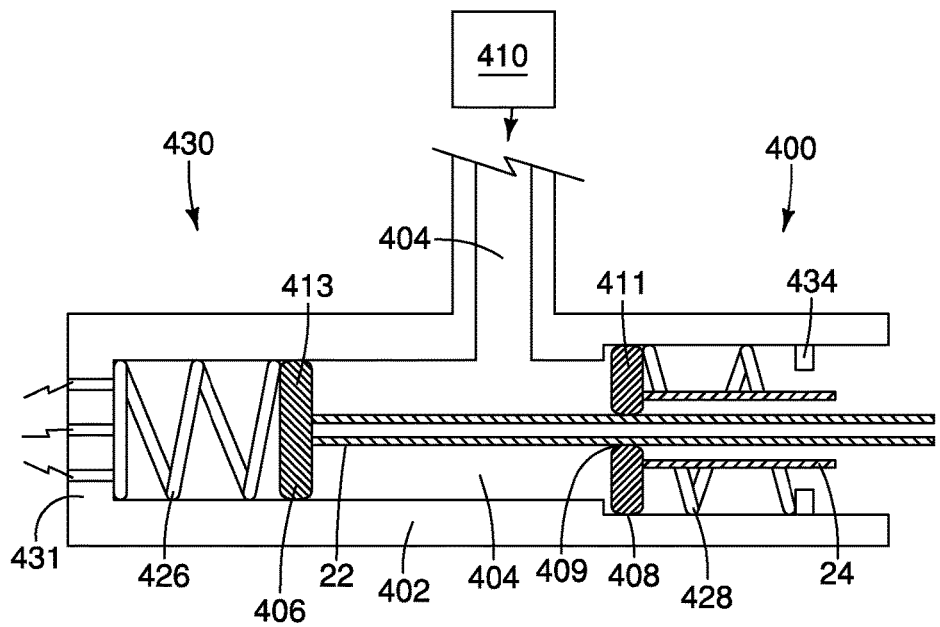
FIG. 7 is a sectional view of an embodiment of a control mechanism according to an embodiment of the present invention.
Figure 8:
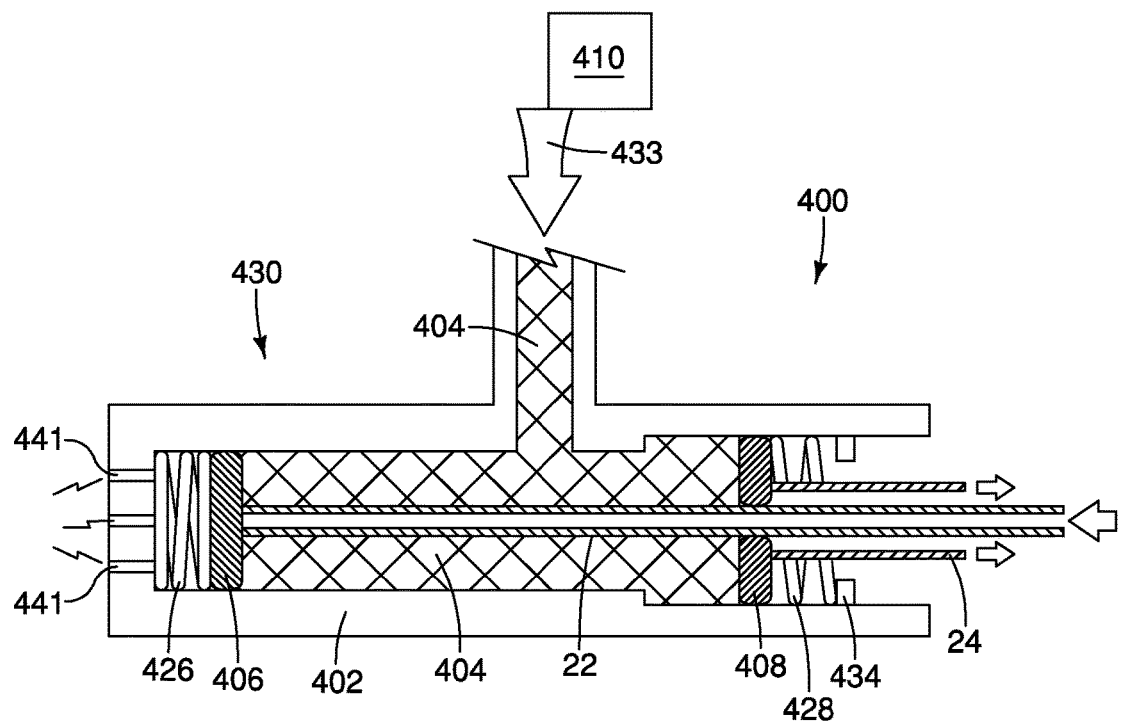
FIG. 8 is a sectional view of the control mechanism shown in FIG. 6 in a second position.

An embodiment of a control system 400 is shown in FIGS. 7 and 8. The control system 400 may be provided as part of the handle 26 at the proximal portion 27 of the stent delivery system 10. The control system 400 includes a housing 402 having a chamber 404 formed therein.

The control system 400 further includes a first drive 406 positioned within the housing 402 and operably connected to the inner shaft 22. The control system 400 includes a second drive 408 positioned within the housing 402 operably connected to the outer shaft 24. The inner shaft 22 extends through an opening 409 in the second drive 208 and coaxially through the outer shaft 24. The opening 409 may be sized and shaped to form a fluid tight seal against the inner shaft 22 and allow the inner shaft 22 to move proximally and distally in response to the pressure changes. The first and second drives 406, 408 may be provided in the form of a piston that forms a seal against the chamber 404. In some embodiments, an outer diameter 411 of the second drive 408 may be larger than an outer diameter 413 of the first drive 406 to equalize the force on the first and second drives 406, 408. Friction may also be considered in equalizing the force on the first and second drives 406, 408. In the embodiments where the stent 28 is expanded and collapsed by movement of the inner and outer shafts 22, 24 in equal and opposite directions, the force on the first and second drives 406, 408 is substantially equal.

A pressure controller 410 is operably connected to the housing 402 and the chamber 404 and may be provided as a flexible membrane, a syringe, a balloon device as described above or any other type of pressure controller that is capable changing the pressure within the chamber 404. A first biasing member 426 is shown positioned between a wall 431 of the chamber 404 and the first drive 406. A second biasing member 428 is shown positioned between the second drive 208 and a stop 434 formed in the housing 402. As shown in FIGS. 7 and 8, the biasing member 426, 428 may be provided as compression springs. In the absence of pressure within the chamber 404, the first and second biasing members 426, 428 bias the drives toward each other so that the control system 400 is in a first position 430 with the drives 406, 408 relatively close together. In the first position 430 of the control system 400, the stent is in the constrained configuration 40 shown in FIG. 1A.

As shown in FIG. 8, external pressure indicated by the arrow 433 may be provided from the pressure controller 410 to provide pressure against the first and second drives 406, 408 to move the control system 400 from the first position 430 (shown in FIG. 7) to a second position 440 with a single-handed operation. The second position 440 for the control system 400 corresponds to the expanded configuration 60 of the stent 28 shown in FIG. 1B. As shown in FIG. 8, with the pressure in the chamber 404 increased due to the external pressure on the pressure controller 410, the first and second drives 406, 408 move apart and move the inner shaft 22 and outer shaft 24 in opposite directions to remove longitudinal tension on the stent 28 and expand the stent 28 into the expanded configuration 60. As indicated by the arrows in FIGS. 1B and 8, the inner shaft 22 is moved proximally and the outer shaft 24 is moved distally and longitudinal tension on the stent 28 is relaxed. The stent 28 may be repeatedly moved between the constrained configuration 40 and the expanded configuration 60 by changing the pressure on the pressure controller 410 to change the pressure within the chamber 404. The housing 402 may also include one or more openings 441 to allow air within the chamber 404 to escape or enter in response to movement of one or both drives 406, 408.

Similar to the control system 300, the control system 400 may also be provided with the first and second biasing members 426, 428 in the form of tension springs. One skill in the art would understand that the tension springs would be positioned on the opposite sides of the drives 406, 408 than shown in FIGS. 7 and 8.

In addition, the control system 400 may include a releasable locking mechanism (not shown) that holds the control system 400 in the second position 440 until the stent delivery system 10 is in position within a patient's lumen and the stent 28 is in a position to be moved to the expanded configuration 60. Any type of locking mechanism may be used to releasably lock the control mechanism 400 in the first configuration 430 and the second configuration 440 as will be understood by one skilled in the art.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A control system for controlling movement of a stent delivery system having a first shaft and a second shaft, the second shaft movable relative to the first shaft, the control system comprising:
a housing having a chamber formed therein;
a first drive at least partially positioned and movable within the housing and operably connected to the first shaft, the first drive being movable in response to a change in pressure within the chamber, the first drive contacting a first portion of an interior wall of the housing and forming a first seal;
a second drive at least partially positioned and movable within the housing and operably connected to the second shaft, the second drive being movable in response to the change in pressure within the chamber, the second drive contacting a second portion of the interior wall of the housing and forming a second seal;
a pressure controller operably connected to the housing the pressure controller changing the pressure within the chamber to move the second drive relative to the first drive;
a first spring biasing the first drive; and
a second spring biasing the second drive;
wherein movement of the second drive relative to the first drive in a first direction causes the second shaft to move relative to the first shaft to expand a stent operably connected thereto and movement of the second drive relative to the first drive in a second direction causes the second shaft to move relative to the first shaft to reconstrain the stent from an expanded configuration to a constrained configuration.

2. The control system of claim 1, wherein in the second direction is in an opposite direction to the first direction.

3. The control system of claim 1, wherein the pressure controller comprises a syringe.

4. The control system of claim 1, wherein the pressure controller comprises a flexible membrane.

5. The control system of claim 1, wherein the pressure controller comprises a balloon device.

6. The control system of claim 1, further comprising a belt operably connected to the first drive and the second drive.

7. The control system of claim 1, wherein the first shaft extends through the second drive and coaxially with the second shaft.

8. The control system of claim 1, wherein the housing is provided within a handle.

9. The control system of claim 1, wherein the first drive and the second drive move relative to each other in substantially equal and opposite directions in response to the pressure controller changing the pressure.

10. The control system of claim 1, wherein the first drive and the second drive are at least partially positioned and movable within the chamber formed in the housing.

11. The control system of claim 1, wherein the housing further comprises a stop adapted to limit the movement of the first drive or the second drive.

12. A stent delivery system comprising:
a first shaft;
a second shaft, the second shaft movable relative to the first shaft and coaxially extending within the first shaft;
a stent having a first end portion operably connected to the first shaft by a first constraining member and a second end portion operably connected to the second shaft by a second constraining member so that the first and second constraining members, in response to movement of the second shaft to the first shaft, apply a longitudinal tension to or release the longitudinal tension from the first end portion of the stent and the second end portion of the stent; and a control system comprising:
- a housing having a chamber formed therein;
- a first drive at least partially positioned and movable within the housing and operably connected to the first shaft;
- a second drive at least partially positioned and movable within the housing and operably connected to the second shaft;
- a biasing member, the biasing member comprising a spring: and
- a pressure controller operably connected to the housing, the pressure controller changing the pressure within the chamber and to move the second drive relative to the first drive so that movement of the second drive relative to the first drive in a first direction causes the second shaft to move relative to the first shaft to expand the stent operably connected thereto and movement of the second drive relative to the first drive in a second direction causes the second shaft to move relative to the first shaft to reconstrain the stent from an expanded configuration to a constrained configuration so that the longitudinal tension is applied to the first end portion and the second end portion of the stent in the constrained configuration by movement of the second drive relative to the first drive in the second direction.

13. The delivery system of claim 12, wherein the first drive is movable in a first direction and the second drive is movable in an opposite direction to the first direction to change the longitudinal tension on the stent.

14. The control system of claim 12, wherein the first drive and the second drive are at least partially positioned and movable within the chamber formed in the housing.

15. The control system of claim 12, wherein the housing further comprises a stop adapted to limit the movement of the first drive or the second drive.

* * * * *